United States Patent [19]

Brooks, Jr.

[11] 4,120,166
[45] Oct. 17, 1978

[54] CEMENT MONITORING METHOD
[75] Inventor: Fred A. Brooks, Jr., Houston, Tex.
[73] Assignee: Exxon Production Research Company, Houston, Tex.
[21] Appl. No.: 781,087
[22] Filed: Mar. 25, 1977
[51] Int. Cl.² .............................................. E02B 17/00
[52] U.S. Cl. ................................. 405/225; 166/253; 324/65 P; 405/227
[58] Field of Search .......................... 61/100, 86, 98; 166/253, 66, 250; 52/1, 169.1; 324/9, 65 P

[56] References Cited
U.S. PATENT DOCUMENTS

| | | | |
|---|---|---|---|
| 2,068,535 | 1/1937 | Crandall | 166/253 X |
| 2,171,840 | 9/1939 | Armentrout et al. | 166/253 |
| 3,319,158 | 5/1967 | McDoulett et al. | 324/9 |
| 3,489,219 | 1/1970 | Higgins | 166/253 |
| 3,878,687 | 4/1975 | Tragesser | 61/100 |
| 3,987,636 | 10/1976 | Hruska et al. | 61/100 |

Primary Examiner—Dennis L. Taylor
Attorney, Agent, or Firm—Salvatore J. Casamassima; Robert L. Graham

[57] ABSTRACT

A method for monitoring the location and set of a cement slurry within a support member of an offshore structure is disclosed. The location and setting properties of the cement are determined by monitoring the electrical resistivity of the fluid within the support member. Preferably, a plurality of electrical probes mounted along the length of the support member can be used to measure the electrical resistivity of fluid within the member. Normally, the presence of cement would be indicated by an abrupt change of resistivity as the cement displaces the original fluid (air or sea water) present in the support member. Resistivity of the cement slurry will also change gradually as the cement sets.

3 Claims, 6 Drawing Figures

CEMENT MONITORING METHOD

BACKGROUND OF THE INVENTION

1. Field of the Invention

This invention relates to the grouting of tubular and support members of offshore structures used in the oil and gas industry.

2. Description of the Prior Art

The search for oil and gas has extended into the deep, rough waters of the outer continental shelf areas. To conduct drilling and production operations in such offshore areas it has become necessary to employ the use of larger and more sophisticated offshore platforms.

Although fixed offshore platforms are of varying sizes and designs, most are installed at their offshore locations by the same general technique. Normally, the platform which is a support structure fabricated onshore, is towed to an offshore location where it is flooded and allowed to settle in an upright position. When uprighted, the legs of the platform will usually settle a short distance into the sea floor. However, it is necessary to give the platform additional support by driving a pile through the platform legs and into the sea floor. The annulus defined by the pile and the platform leg is then filled with cement to form a bond between the leg and the pile. Grouting of the annulus in this manner secures the platform to the sea floor and adds weight to the platform, thereby enhancing its stability in rough waters.

During grouting of the platform legs several problems can arise which would result in faulty or inadequate cementing. The most serious problem is lost circulation which occurs when the weight exerted by the annular column of cement forces the cement into the soft or weakly consolidated formations surrounding the platform leg. With cement escaping into the formation, circulation is lost and the annulus surrounding the platform leg cannot be filled. Another potential problem is improper setting of the cement. Maximum strength and support is given to the platform legs only if the cement is properly cured. Contaminants such as sea water or entrained air can alter the setting properties of the cement resulting in a weakened bond between the pile and platform leg.

In order to detect problems arising during grouting operations it is necessary to monitor the location and setting of the cement. For example, cementing would be halted once the cement reaches a predetermined level within the platform leg that would give the leg adequate support. Failure of the cement to reach certain levels after known volumes had been pumped would be indicative of either lost circulation or a mechanical failure within the platform leg such as packer failure. Likewise, monitoring the set of the cement would indicate whether the cement is curing at a proper rate and whether it is uncontaminated.

With the very tall platforms that are now being used it is becoming increasingly difficult to properly monitor the grouting operation as it is taking place. Manual inspection by divers becomes unfeasible when water depths exceed diver capabilities. Remote visual inspection by subsea vehicles or submerged television cameras is expensive and does not provide any information relating to the setting of the cement. Temperature measuring probes located within the walls of the platform have been used to detect cement location but these probes have not always been reliable because the temperature of the cement tends to rapidly equilibrate with the temperature of the surrounding sea water.

Thus there exists a need in the art for a reliable cement detection and monitoring system which accurately indicates the location and setting of cement used in grouting offshore platform legs.

SUMMARY OF THE INVENTION

The present invention overcomes the problems unresolved by the prior art and provides a method for rapidly and accurately determining the location and set of cement during the grouting of an offshore structure. Broadly, the method involves strategically monitoring the electrical resistivity of the fluid within the support member of the offshore structure that is being grouted. Means for measuring electrical resistivity of fluids such as electrical probes mounted along the length of the support member, can be used to monitor the fluid within the support member at a plurality of points.

Most applications of the present invention would involve grouting the annulus formed between the leg of an offshore platform and the pile driven through the leg. As the annulus, fills with cement slurry the slurry would contact the probe or probes located within the leg. The presence of cement would normally be indicated by an abrupt change of resistivity detected by the probe. For example, if sea water is the original fluid in the annulus then resistivity will sharply increase as high resistivity cement slurry displaces the low resistivity sea water. Once the annulus has been filled with cement the setting characteristics of the cement can be monitored as the cement cures. As the cement sets the resistivity of the cement slurry will gradually increase. Comparison of the resistivity measurements obtained during the monitoring operation with known set versus resistivity standards will indicate whether the cement is curing properly. Unusual or inconsistent resistivity measurements can reveal the presence of contaminants in the cement slurry which may inhibit the rate of set or cause inadequate strength development.

DESCRIPTION OF THE PREFERRED EMBODIMENT

Figure 1:
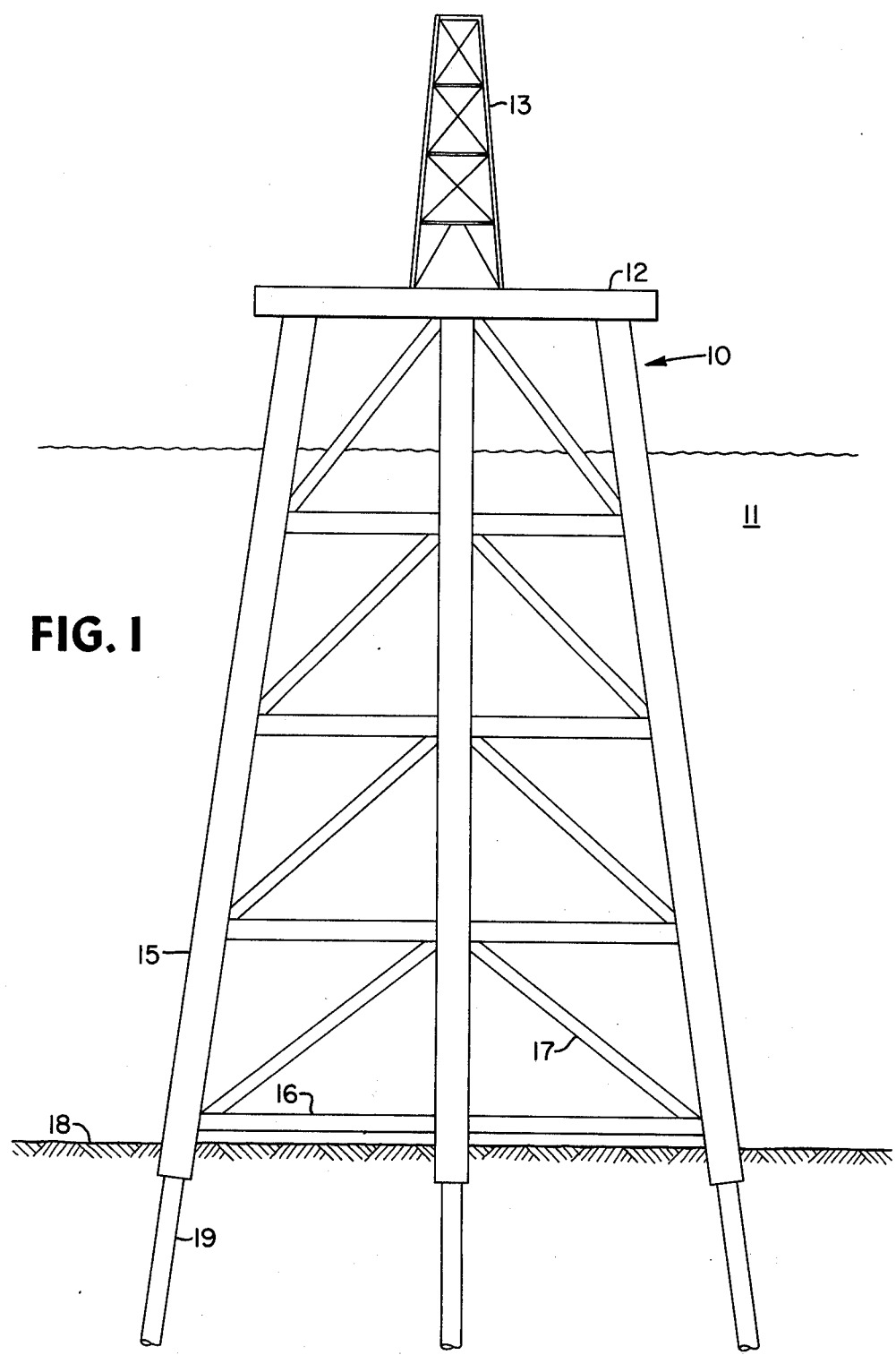
FIG. 1 is an elevational view of a typical offshore structure.

Referring to FIG. 1 of the drawings, an offshore platform 10 is shown positioned at a drill site in a body of water 11. Platform 10 is a fixed, bottom supported structure tyical of those used for offshore drilling and production. Platform deck 12 supports drilling derrick 13 and associated drill rig equipment (not shown). Platform 10 is fabricated from a plurality of welded support members including legs 15, cross braces 16 and diagonal braces 17.

Legs 15 are large diameter tubular members which provide the greatest amount of support for platform 10. When platform 10 is uprighted in the position shown, the weight of the structure will cause the legs to sink a short distance into sea floor 18. The depth to which the legs will sink will depend a great deal on the porosity and strength of the substrate. In any event, the legs must be more securely anchored to the sea floor to provide the platform with a high degree of stability. Anchoring is accomplished by driving pile 19 through legs 15 and into sea floor 18 to a predetermined depth. The piles are normally made of tubular steel and are sized to readily pass through the platform legs.

Figure 2:
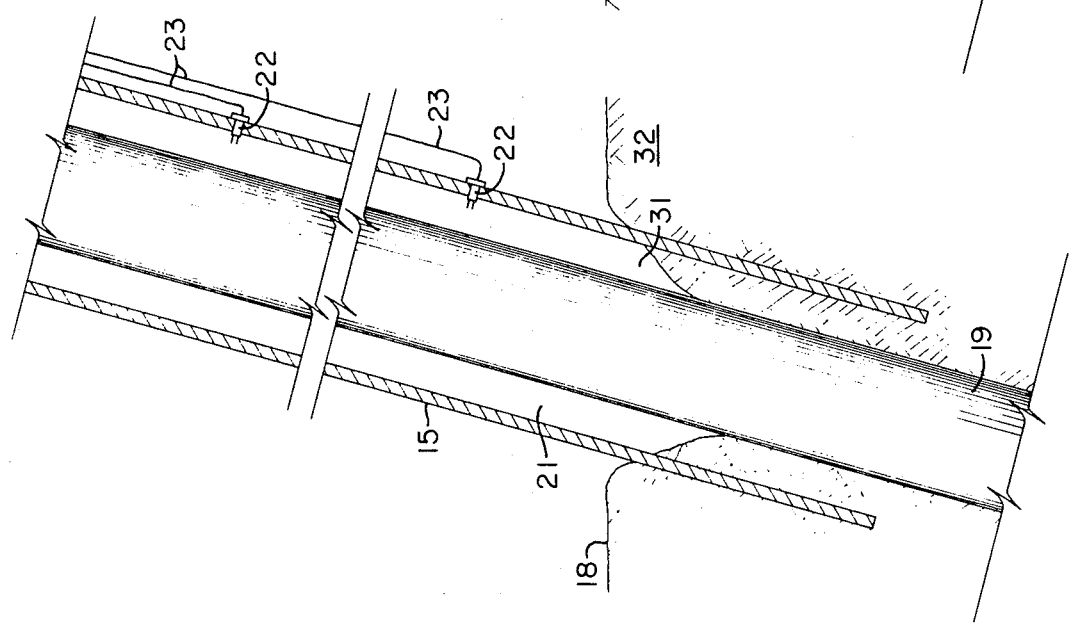

FIG. 2 illustrates by means of an enlarged cross-sectional view, the passage of pile 19 through leg 15 into sea floor 18. As shown, an annular space 21 exists between leg 15 and pile 19. It is this annular space which must be grouted by cement to form a secure bond between the leg and the pile and to provide the platform with additional rigidity and stability. The cement also displaces the air and sea water from within the annulus and serves to protect the piling and the inside of the platform leg against corrosion. Cross braces 16 and diagonal braces 17 shown in FIG. 1 can also be filled with cement to further add to the stability of the platform; however, this is normally not standard practice.

Secured within the walls of platform leg 15 are electrical probes 22. The probes are exposed to annular space 21 and may be welded or threadably inserted into leg 15. Two probes are shown in FIG. 2, but a plurality of probes disposed along the length of each of the platform legs can be employed. It is necessary that probes 22 be properly secured and tightly sealed to preserve the electrical integrity of the circuit.

Figure 5:
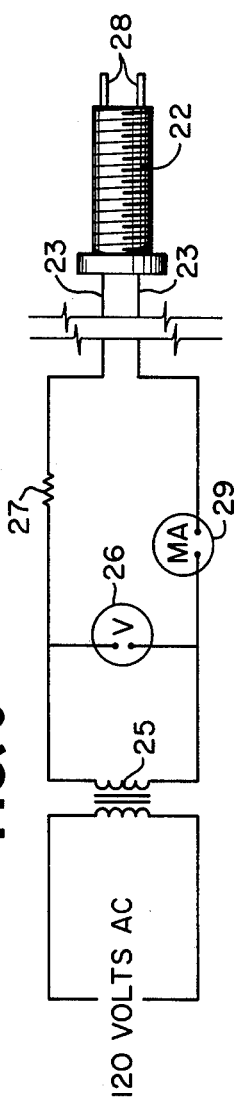
FIG. 5 shows an electrical circuit diagram for a cement detection probe suitable for use in the method of the present invention.

Probes 22 are electrically connected to the surface with electrical cables 23 and are used to measure the resistivity or conductivity of the fluid within annular space 21 to which they are exposed. A simple ohmmeter circuit particularly useful in measuring resistivity in saline environments is diagramatically shown in FIG. 5. An alternating current source such as a 120 volt AC source is stepped down by means of transformer 25 to a low voltage output of about 7 or 8 volts as recorded on voltmeter 26. Resistor 27 is shown to indicate the lead resistance created by cable 23 in transmitting current down the platform leg to probe 22 and back. Probe 22 can be a standard threaded electrical connector having a pair of electrodes 29 across which the current must flow to complete the circuit. The resistance across the electrodes will be solely determined by the resistivity of the fluid to which the electrodes are exposed. Milliameter 29 can be used to measure the returning current from which resistance across electrodes 28 can be calculated. The use of an AC driving source eliminates electrode degradation problems caused by the electrolytic effect created when the electrodes are immersed in a saline fluid such as sea water. Use of a DC source would, in effect, render the probe a battery, resulting in electrolysis of the sea water and rapid degradation of the electrodes.

Figure 4:
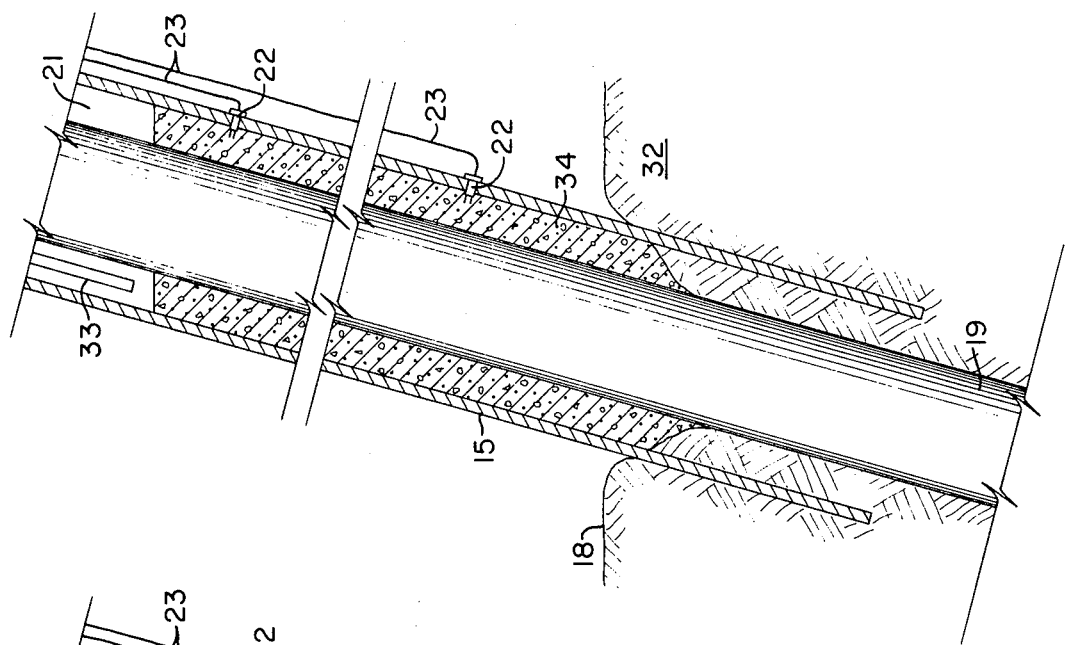
FIGS. 2, 3 and 4 are enlarged cross-sectional views of one of the legs of the offshore structure showing the sequential operation of grouting the legs.
Figure 3:
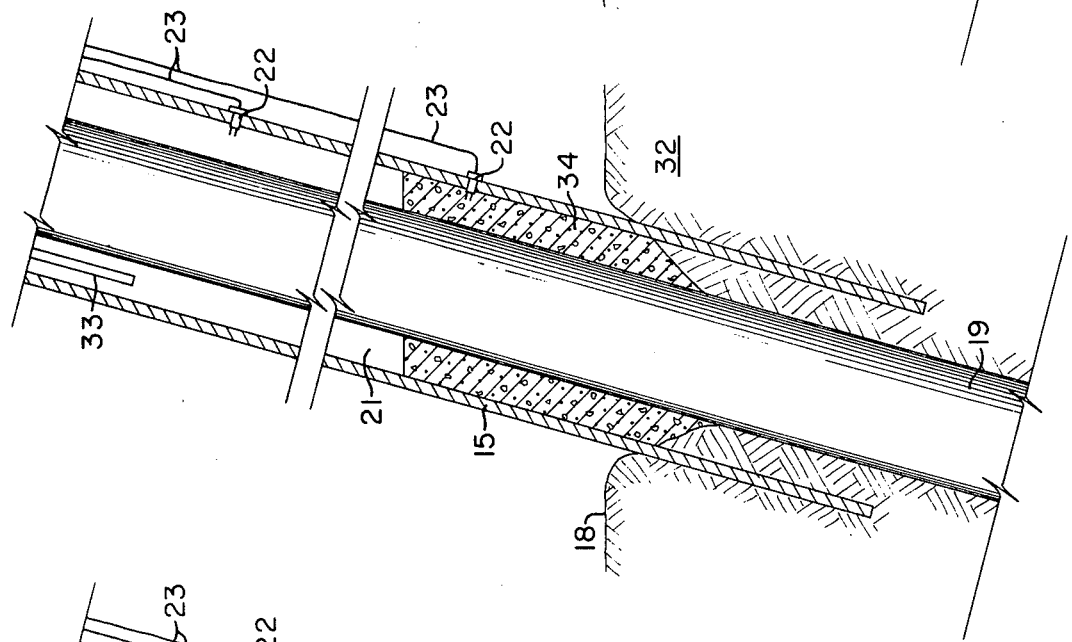

FIGS. 2, 3 and 4 sequentially depict how probes 22 may be utilized to locate the position of the cement slurry as it fills annular space 21 during a grouting operation and how they may be used to monitor the set of the cement once the annulus is filled. Initially, as shown in FIG. 2, annular space 21 is filled with sea water or air, depending on whether leg 15 was deballasted to upright the platform. The annulus may extend somewhat below sea floor 18 because of void space 31 which is created by the compaction of substrate formation 32 under the impact of pile 19 as it is driven into the formation. This void space, must also be grouted to ensure maximum platform support.

FIG. 3 shows annular space 21 partially filled with cement slurry 34. The slurry may be deposited in the annulus by means of a narrow tubing string 33, also known as a "macaroni" string, which is lowered down the annulus. Alternatively, a pipe (not shown) along the outside of the platform leg may be used to feed cement into the leg. As the cement slurry fills the annulus it displaces the fluid originally within the annulus. Once the slurry passes lower probe 22 a substantial change in resistivity will be recorded by the probe indicating that the cement slurry has reached the level at which the probe is located. For example, if sea water is the fluid originally in annulus then probe 22 will register about a two to five-fold increase in resistivity as the sea water is displaced by the cement slurry. This is because the salinity of sea water makes it a much better electrical conductor than the substantially non-electrolyte cement slurry. Conversely, if air was within the annulus then the passage of the slurry past the probe would result in a substantial decrease in resistivity, the cement slurry being much more conductive than air. In this manner, as the slurry fills annular space 21, its level within the annulus can be accurately tracked by a plurality of strategically placed probes located along the length of leg 15. The probes also serve as early warning devices in the event lost circulation occurs as a result of fracturing or fissuring of substrate formation 32. Failure of cement slurry to reach a certain probe after a known volume of slurry had been pumped into the leg or a return of resistivity to original levels indicating fallback of the slurry below a probe, would be a clear warning that a lost circulation problem had occurred.

Referring now to FIG. 4, annular space 21 has now been filled with additional quantities of cement slurry. Once again as the slurry passes upper probe 22 a substantial change in fluid resistivity will be recorded. Assuming upper probe 22 is at the level at which grouting is to be stopped, then the resistivity change indicated by probe 22 will signal a halt in pumping cement slurry down tubing string 33. With all of the cement slurry emplaced, probes 22 can then be used to monitor the slurry as it sets. As cement cures to a hardened state the activity of the mobile ions present in the cement slurry gradually reduces with time. As a result, the resistivity of the cement increases during the setting process as ionic mobility slackens. Probes 22 will, therefore, indicate this change in resistivity. Comparing the monitored resistivity data with standardized or control figures for the cement being used will reveal whether the cement slurry is setting properly. Monitoring all of the probes is essential since the cement initially pumped into the platform leg will set sooner than the final quantities of slurry that were pumped. In addition, there may be pockets of improperly setting cement located along the length of the leg that might go undetected should only one or two probes be monitored.

Although the above discussion relates to the grouting of the annulus between a platform leg and pile, the method of the present invention is equally applicable to the grouting of any of the supporting members of an offshore platform. For example, referring back to FIG. 1, probes can also be inserted within cross braces 16 and diagonal braces 17 should it be necessary to grout those tubular members as well as leg 5. Thus the present invention should be broadly construed as a remote detection and monitoring method applicable to the grouting of any support member of an offshore platform. It should be understood that several variations and modifications may be made in the embodiments described herein without departing from the broad inventive concept disclosed herein.

FIELD TESTS

An offshore platform installed in the Santa Barbara Channel off the coast of Southern California was grouted using the detection and monitoring method of the present invention. The offshore platform was first towed in two sections to the drill site which was located in 850 feet of water. After the two main sections of the platform were attached, the legs of the platform were ballasted causing the platform to upright itself on the ocean floor. The total height of the platform from base to the top of the leg jacket was 865 feet. Soon thereafter grouting operations were commenced in the main legs of the platform. The cement used for grouting was an expansive Portland cement sold under the trade name Victor Chemstress II by Southwest Portland Cement Co., which contained 1% calcium chloride.

Figure 6:
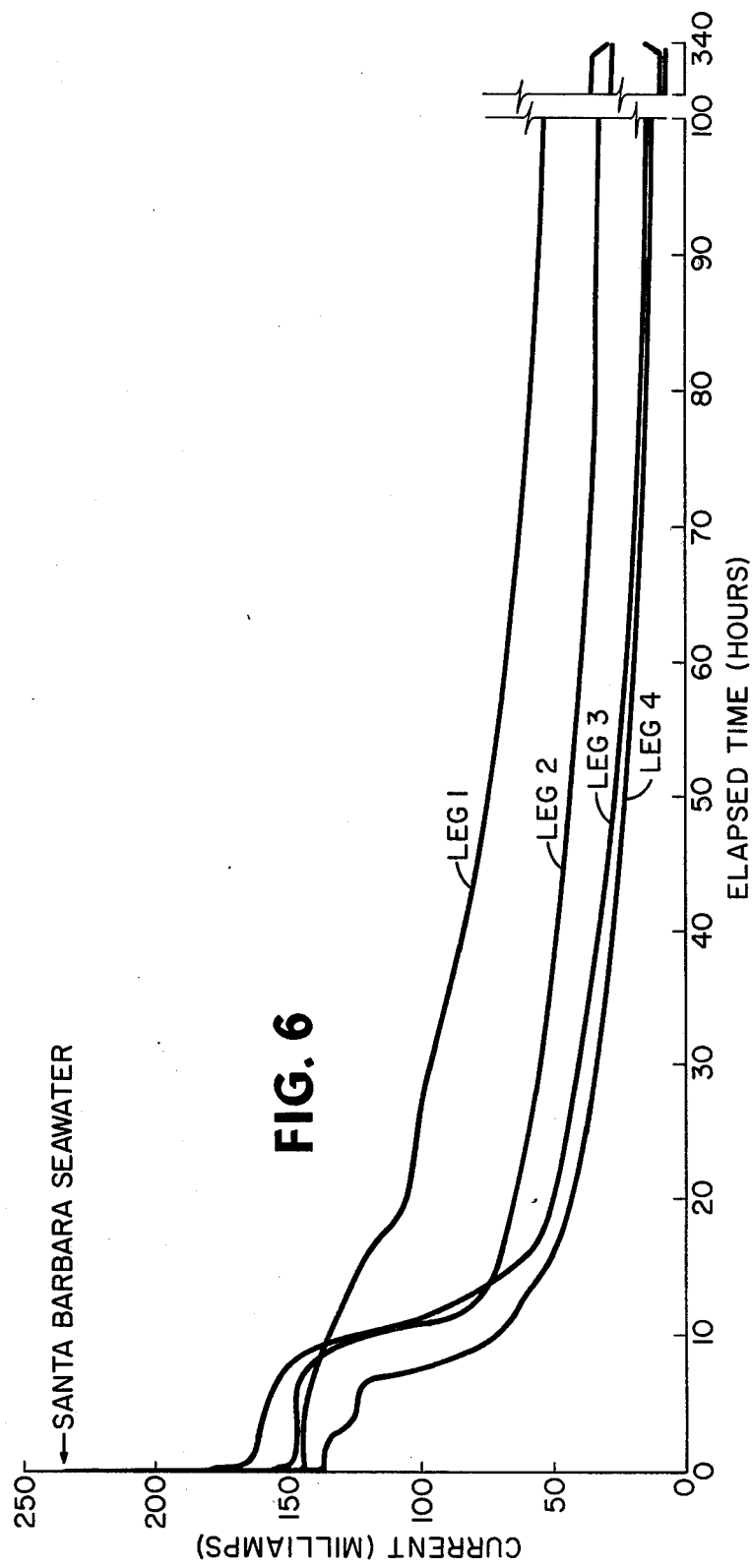
FIG. 6 shows typical current curves measured with the use of the detector of FIG. 5 during grouting operations of the legs of an offshore platform.

During grouting operations the method of the present invention was tested on the eight main platform legs and twelve skirt legs. Probes, installed in each leg, were used to monitor the grouting operation. Typical results of the tests appear in FIG. 6 which shows current (in milliamps) plotted against time. The test results can be converted to resistance simply by dividing the voltage of the system (approximately 7.5 volts) by the recorded amperage. It should be emphasized that the term "resistivity" is being broadly used in this specification to encompass any units of electrical measurement that can be readily converted to or read as units of electrical resistance (ohms) or conductance (mhos). The circuit for the detection probe used in the tests was identical to the one shown in FIG. 5.

Interpreting the results is straightforward. At zero elapsed time the current passing through the sea water originally in each platform leg was 235 milliamps. The quantum drop in current commencing from zero elapsed time indicate that the cement slurry has passed the level at which the probe is located within the leg. Note that for legs 2 and 3 a slight increase in current occurs just after the initial decrease. This initial increase in conductivity is caused by intermixing of the sea water with some of the soluble, ionic components of the cement. With the exception of Leg 1, all of the probes recorded a gradual but sharp decline in current over the first 10 to 15 hours, indicating that the initial setting of the cement was taking place. After about 20 hours, a slow, almost imperceptible, decline in current takes place over the next 50 or 60 hours. This indicates that although the cement is essentially set, it is now beginning to develop measurable strength. For the cement used, strength above 100 psi occurs after about 12 hours of setting.

The nontypical behavior recorded for leg 1 indicates that the cement slurry was slightly contaminated with sea water resulting in a much slower initial rate of set. However, after about 100 hours of setting time all probes showed a leveling off to an almost constant amperage indicating that the cement in each leg had almost completely set.

What is claimed is:

1. In the cementing of an offshore tubular support member having a pile positioned therein, a method for determining the degree of set of the cement, which comprises:
    (a) securing a probe capable of measuring the electrical resistance of fluid at a fixed elevation in the annulus defined by said support member and said pile,
    (b) upwardly displacing fluid in said annulus with a cement slurry until said slurry reaches an elevation above said probe as indicated by a change in the electrical resistance measured by said probe, and
    (c) monitoring the electrical resistance of said cement slurry measured by said probe for a time period sufficient to indicate set of the cement.

2. The method as defined in claim 1 wherein said probe includes two spaced apart electrodes exposed to fluid in said annulus and means for imposing an alternating current flow across said electrodes.

3. In the cementing of an offshore tubular member having a pile positioned therein, a method for determining the location and degree of set of cement used in the cementing operation which comprises:
    (a) securing lower and upper probes to said tubular member, said lower probe being positioned on the tubular member at the minimum elevation that the cement must attain therein, and said upper probe being positioned on said tubular member at an elevation substantially above said lower probe, each of said probes including spaced apart electrodes exposed to fluid in the annulus defined by said pile and said tubular member;
    (b) imposing an alternating current flow between the electrodes of each probe;
    (c) monitoring the resistance of the alternating current flowing between the electrodes of each of said probes;
    (d) upwardly displacing the fluid in said annulus with a cement slurry until the cement slurry reaches an elevation at least above said lower probe as indicated by a change in the electrical resistance between the electrodes thereof; and
    (e) continuing monitoring the electrical resistance of the alternating current flowing between said electrodes of the probes located below the top of the cement attained by step (c) for sufficient time to indicate set of the cement.

* * * * *